(12) United States Patent
McGroary et al.

(10) Patent No.: US 9,844,636 B2
(45) Date of Patent: Dec. 19, 2017

(54) PRESSURE SUPPORT DEVICE USER INTERFACE

(75) Inventors: Paul Denis McGroary, Gibsonia, PA (US); Michele Marut, White Plains, NY (US); Joshua Mark Greenberg, Pittsburgh, PA (US); Hugh M. Dunn, Pittsburgh, PA (US); Mike Daikubara, Quincy, MA (US); Kenneth E. Cole, New Alexandria, PA (US); Timothy James Dixon, Trafford, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 755 days.

(21) Appl. No.: 13/148,751

(22) PCT Filed: Jan. 22, 2010

(86) PCT No.: PCT/IB2010/050290
§ 371 (c)(1),
(2), (4) Date: Aug. 10, 2011

(87) PCT Pub. No.: WO2010/092496
PCT Pub. Date: Aug. 19, 2010

(65) Prior Publication Data
US 2011/0308518 A1 Dec. 22, 2011

Related U.S. Application Data

(60) Provisional application No. 61/152,466, filed on Feb. 13, 2009.

(51) Int. Cl.
*A61M 16/00* (2006.01)
*A61M 15/00* (2006.01)
(Continued)

(52) U.S. Cl.
CPC ........ *A61M 16/0051* (2013.01); *A61M 16/16* (2013.01); *A61M 2205/502* (2013.01)

(58) Field of Classification Search
None
See application file for complete search history.

(56) References Cited

U.S. PATENT DOCUMENTS 3,584,401 A 6/1971 Cryer
4,495,944 A * 1/1985 Brisson et al. ............... 600/538
(Continued)

FOREIGN PATENT DOCUMENTS

DE 9317450 U1 6/1994
EP 0893750 A1 7/1998
(Continued)

*Primary Examiner* — (Jackie) Tan-Uyen T Ho
*Assistant Examiner* — Eric Bryant
(74) *Attorney, Agent, or Firm* — Michael W. Haas (57) ABSTRACT

A pressure support device such as a CPAP machine, is provided, which includes a housing, and a controller enclosed by the housing. The controller operates the CPAP machine independently or in combination with an accessory such as, for example and without limitation, a humidifier. A user interface is operably coupled to the controller and includes a primary display, a secondary display and a single control. The single control is operable in a first mode of operation to adjust operating parameters of the CPAP machine, and in a second mode of operation to adjust operating parameters of the humidifier. The secondary display preferably comprises a dead front, which is operational (e.g., without limitation, visible) only in the second mode of operation. A method of operating a pressure support device is also disclosed.

16 Claims, 7 Drawing Sheets

(51) Int. Cl.
*F16K 31/02* (2006.01)
*A61M 16/16* (2006.01)

(56) References Cited

U.S. PATENT DOCUMENTS

| | | | |
|---|---|---|---|
| 5,237,987 A | | 8/1993 | Anderson et al. |
| 5,452,714 A | * | 9/1995 | Anderson et al. ....... 128/205.11 |
| 5,634,154 A | * | 5/1997 | Sasagaki et al. .............. 396/291 |
| 6,050,260 A | * | 4/2000 | Daniell et al. ........... 128/204.22 |
| 6,096,985 A | * | 8/2000 | Ritter et al. .................. 200/6 A |
| 6,667,726 B1 | * | 12/2003 | Damiani et al. ................ 345/1.1 |
| 6,694,974 B1 | * | 2/2004 | George-Gradon et al. ........................ 128/203.17 |
| 7,051,735 B2 | * | 5/2006 | Mechlenburg et al. . 128/204.21 |
| 2003/0230308 A1 | * | 12/2003 | Linden ..................... 128/204.18 |
| 2004/0055597 A1 | * | 3/2004 | Virr et al. ................ 128/203.12 |
| 2004/0118403 A1 | * | 6/2004 | O'Connor et al. ...... 128/204.23 |
| 2006/0213518 A1 | * | 9/2006 | DeVries et al. ......... 128/204.21 |
| 2007/0062533 A1 | * | 3/2007 | Choncholas et al. .... 128/204.23 |
| 2007/0204225 A1 | * | 8/2007 | Berkowitz ........... G11B 19/025 715/700 |
| 2008/0000474 A1 | | 1/2008 | Jochle |
| 2010/0229867 A1 | * | 9/2010 | Bertinetti et al. ....... 128/205.25 |
| 2011/0025488 A1 | * | 2/2011 | Leon ...................... B60K 37/06 340/456 |

FOREIGN PATENT DOCUMENTS

| | | |
|---|---|---|
| EP | 1374938 A1 | 1/2004 |
| JP | 2003506161 A | 2/2003 |
| JP | 2008517682 A | 5/2008 |
| WO | WO0110489 A2 | 2/2001 |
| WO | 2004112873 A1 | 12/2004 |
| WO | 2007019628 A1 | 2/2007 |
| WO | WO2008056993 A2 | 5/2008 |
| WO | 2009059359 A1 | 5/2009 |

* cited by examiner

PRESSURE SUPPORT DEVICE USER INTERFACE

This patent application claims the priority benefit under 35 U.S.C. §119(e) of U.S. Provisional Application No. 61/152,466 filed on Feb. 13, 2009, the contents of which are herein incorporated by reference.

The present invention relates generally to a method and apparatus for controlling a pressure support device and, more particularly, to a user interface having a single control for controlling the pressure support device individually or in combination with an accessory such as, for example, a humidifier.

Figure 1:
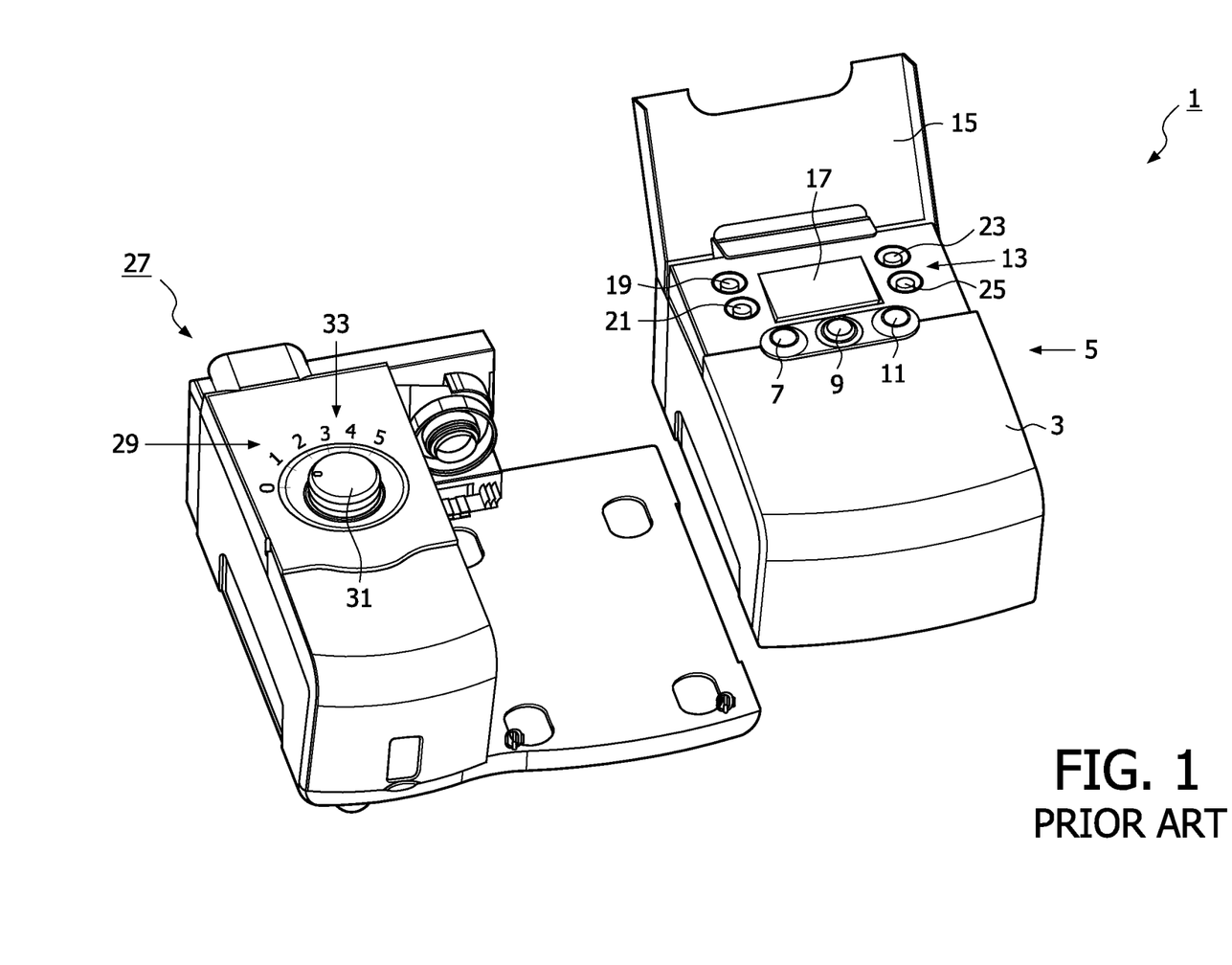
FIG. 1 is a partially exploded isometric view of a pressure support device and a humidifier therefor, also showing the separate user interfaces of the pressure support device and humidifier.

Pressure support devices for providing a flow of breathing gas to an airway of a patient at an elevated pressure to treat a medical disorder, are well known. One basic form of pressure support device is a continuous positive airway pressure (CPAP) machine 1, an example of which is shown in FIG. 1. Specifically, CPAP machine 1 includes housing 3, which encloses a controller (not shown). A user interface 5 is disposed on housing 3 and includes a plurality of independent controls 7, 9, 11 (e.g., without limitation, buttons) for accessing and/or adjusting machine 1 or operating parameters thereof such as, for example and without limitation, the pressure intensity of the gas being delivered to the patient, and the type and/or duration of the therapy being provided. User interface 5 of CPAP machine 1 of FIG. 1 also includes a subpanel 13, which is accessible beneath a cover 15 of machine housing 3. Subpanel 13 includes display 17 and additional controls 19, 21, 23, 25 for adjusting and setting CPAP machine parameters.

CPAP machine 1 is adapted to operate in conjunction with an accessory such as, for example and without limitation, humidifier 27 shown in the example of FIG. 1. Humidifier 27 includes its own user interface 29, which also has a number of separate controls 31 (e.g., without limitation, knob(s)) to adjust humidifier operating parameters 33 (e.g., without limitation, humidity level). Accordingly, one set of controls 7, 9, 11, 19, 21, 23, 25 is required to adjust the operating parameters of CPAP machine 1, and another independent control 31 is required to adjust parameter(s) 33 of humidifier 27.

Among other disadvantages, the numerous different controls 7, 9, 11, 19, 21, 23, 25, 31 can be intimidating and confusing to the user (e.g., patient; caregiver; clinician), making it difficult to ensure that CPAP machine 1 and/or humidifier 27 is/are properly adjusted to provide the appropriate therapy to the patient. Additionally, separate user interfaces 5 and 29 and controls 7, 9, 11, 19, 21, 23, 25 and 31, respectively, of CPAP machine 1 and humidifier 27, respectively, add to the potential confusion and require numerous electrical components (e.g., without limitation, multiple circuit boards (not shown)) increasing the complexity and cost of the pressure support system.

These needs and others are met by embodiments of the invention, which are directed to a user interface and method for controlling a pressure support device, wherein the same single control is operable to control the operating parameters, settings and functions of the pressure support device by itself, or in combination with a suitable accessory such as, for example, a humidifier, when the humidifier is attached to the pressure support device.

As one aspect of the invention, a pressure support device is provided, which is adapted to produce a flow of breathing gas for delivery to a patient. The pressure support device comprises: a housing; a controller enclosed by the housing and being adapted to operate the pressure support device independently or in combination with an accessory; and a user interface being operably coupled to the controller, the user interface comprising a primary display, a secondary display and a single control, the single control being operable in a first mode of operation to adjust a number of operating parameters of the pressure support device, and in a second mode of operation to adjust a number of operating parameters of the accessory, the secondary display being operational only in the second mode of operation.

The single control of the user interface may be a single control knob movably coupled to the housing of the pressure support device. The single control knob may be depressible toward the housing to switch between the first mode of operation and the second mode of operation. The single control knob may also be pivotable clockwise and counterclockwise to adjust a corresponding one of the operating parameters of the pressure support device in the first mode of operation and the operating parameters of the accessory in the second mode of operation.

The primary display may include a number of primary indicia indicative of the operating parameters of the pressure support device, and the secondary display may include a number of secondary indicia indicative of the operating parameters of the accessory. The secondary display may be a dead front, wherein the secondary indicia include a number of illuminable characters disposed on the dead front. The user interface may further comprise a number of illuminating elements, wherein in the first mode of operation the illuminating elements may be inactive such that the illuminable characters are substantially invisible on the dead front, and in the second mode of operation at least one of the illuminating elements may be activated to illuminate a corresponding at least one of the illuminable characters such that it is visible on of the dead front.

The pressure support device may be a CPAP machine, and the accessory may be a humidifier which is adapted to be operably coupled to the housing of the CPAP machine. The second mode of operation may correspond to operation of the CPAP machine in combination with the humidifier, wherein in the first mode of operation the single control of the user interface controls the operating parameters of the CPAP machine, and in the second mode of operation the single control of the user interface controls the operating parameters of the humidifier.

As another aspect of the invention, a method of operating a pressure support device is provided. The method comprises: operably coupling an accessory to the pressure support device; actuating a user interface disposed on a housing of the pressure support device, the user interface comprising a primary display, a secondary display and a single control, the primary display including a number of primary indicia indicative of a number of operating parameters of the pressure support device in a first mode of operation, the secondary display including a number of secondary indicia indicative of a number of operating parameters of the accessory in a second mode of operation, the secondary display being operational only in the second mode of operation; and manipulating the single control of the user interface, the single control being operable to: (a) adjust and select a corresponding one of the operating parameters of the pressure support device in the first mode of operation, (b) adjust and select a corresponding one of the operating parameters of the accessory in the second mode of operation, and (c) switch between the first mode of operation and the second mode of operation.

The method may further comprise automatically detecting the accessory being operably coupled to the pressure support device and, responsive to detecting the accessory, activating the secondary display of the user interface.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise

For purposes of illustration, embodiments of the invention will be described as applied to a CPAP machine employing a humidifier, although it will become apparent that they could also be applied to control a wide variety of medical ventilating devices and/or accessories therefor in addition to, or instead of, a humidifier.

Directional phrases used herein such as, for example and without limitation, upward, downward, inward, outward, clockwise, counterclockwise and derivatives thereof, relate to the orientation of the elements shown in the drawings and are not limiting upon the claims unless expressly recited therein.

The specific elements illustrated in the drawings and described herein are simply exemplary embodiments of the invention. Accordingly, specific dimensions, orientations and other physical characteristics related to the embodiments disclosed herein are not to be considered limiting on the scope of the invention.

As employed herein, the term "accessory" refers to any known or suitable auxiliary device suitable for use in combination with a pressure support device and expressly includes, but is not limited to, a humidifier.

As employed herein, the term "dead front" refers to a portion (e.g., without limitation, panel; surface; face) of a device (e.g., without limitation, pressure support device), which in one mode of operation (e.g., without limitation, a first mode of operation) of the device appears substantially blank and does not perform any function, and in another mode of operation (e.g., without limitation, a second different mode of operation) of the device is functional to display (e.g., show; render visible) a number of indicia corresponding to operating parameters associated with the second mode of operation.

As employed herein, the statement that two or more parts are "coupled" together shall mean that the parts are joined together either directly or joined through one or more intermediate parts. As employed herein, the term "number" shall mean one or an integer great than one (i.e., a plurality).

Figure 2:
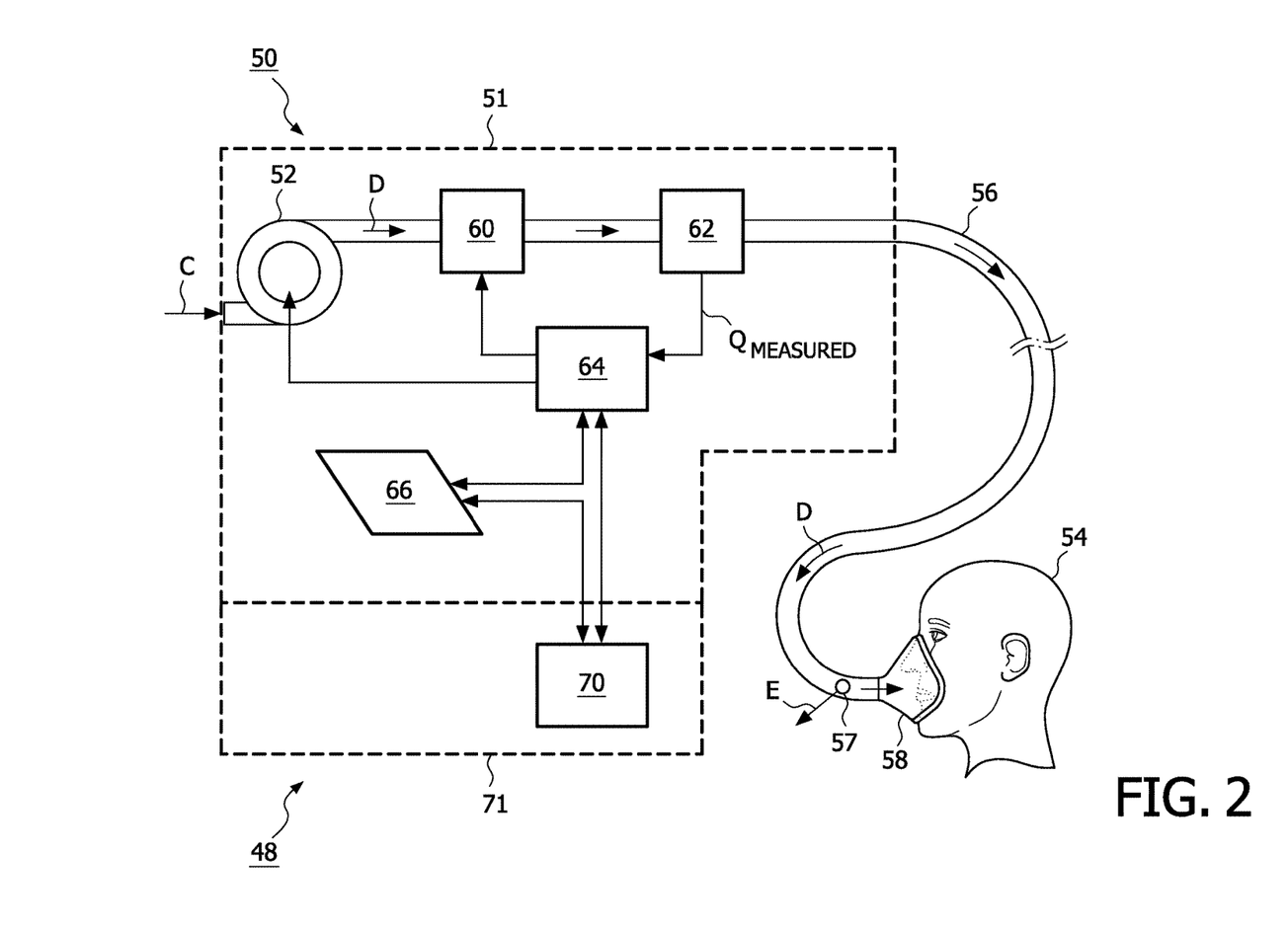
FIG. 2 is a schematic diagram of a pressure support system in accordance with one non-limiting example embodiment of the invention.

FIG. 2 is a schematic diagram of a pressure support system 48 according to one non-limiting embodiment in accordance with the principles of the invention, which will be used herein to illustrate various aspects of the present invention. Specifically, pressure support system 48 includes pressure support device 50, which in the example shown and described herein is a CPAP machine 50. CPAP machine 50 includes housing 51 enclosing gas flow generator 52 (e.g., without limitation, a blower), which receives breathing gas, generally indicated by arrow C, from any suitable source (e.g., without limitation, a pressurized tank of oxygen or air (not shown); the ambient atmosphere; or a combination thereof (not shown)). The gas flow generator 52 generates a flow of breathing gas, such as air, oxygen, or a mixture thereof, for delivery to an airway of patient 54 at relatively higher and lower pressures (e.g., generally equal to or above ambient atmospheric pressure). The pressurized flow of breathing gas, generally indicated by arrow D, is delivered from the gas flow generator 52 via delivery conduit 56 to a breathing mask or patient interface 58 of any known construction, which is typically worn by or otherwise attached to the patient 54 to communicate the flow of breathing gas, D, to the airway of the patient 54. Delivery conduit 56 and patient interface device 58 are typically collectively referred to as a patient circuit. Patient interface 58 preferably includes a pressure sensor operably coupled to controller 64 for measuring the pressure of gas that is delivered to patient 54.

Pressure support system 48 of FIG. 2 is what is known in the art as a single-limb system, meaning that the patient circuit includes only delivery conduit 56 connecting patient 54 to CPAP machine 50. As such, exhaust vent 57 is provided in delivery conduit 56 for venting exhaled gasses from the system, as generally indicated by arrow E. It will be appreciated that exhaust vent 57 can be provided at other locations (not shown) in addition to, or instead of, in delivery conduit 56 such as, for example and without limitation, in patient interface device 58. It will also be appreciated that exhaust vent 57 can have a wide variety of alternative configurations depending on the desired manner in which gas is to be vented from pressure support system 48.

Two-limb systems (not shown), having both a delivery conduit (e.g., 56) and an exhaust conduit (not shown) connected to patient 54, are also contemplated by the present invention. In a two-limb system, the exhaust conduit carries exhaust gas away from patient 54 and includes an exhaust valve at the end distal from patient 54. The exhaust valve in such an embodiment is typically actively controlled to maintain a desired level or pressure in the system, which is commonly known as positive end expiratory pressure (PEEP).

In the example embodiment shown in FIG. 2, patient interface device 58 is a nasal mask. It will be appreciated, however, that patient interface device 58 can include a nasal/oral mask, nasal pillows, tracheal tube, endotracheal tube, or any other known or suitable device that provides a suitable gas flow communicating function. For purposes of the present invention, the phrase "patient interface" includes delivery conduit 56 and any other structures that connect the source of pressurized breathing gas, D, to patient 54.

In the illustrated embodiment, pressure support system 48 includes a pressure controller in the form of a valve 60 provided in delivery conduit 56. Valve 60 controls the pressure of the flow of breathing gas, D, from flow generator 52 delivered to patient 54. Flow generator 52 and valve 60 are collectively referred to herein as a pressure generating system because they act in concert to control the pressure and/or flow of gas, D, delivered to patient 54. However, it will be appreciated that any other known or suitable alternative technique for controlling the pressure of the gas delivered to patient 54 such as, for example and without limitation, varying the blower speed of flow generator 52, either alone or in combination with a pressure control valve, are contemplated by the present invention. Thus, valve 60 is optional depending on the technique used to control the pressure of the flow of breathing gas, D, delivered to patient 54. If valve 60 is eliminated, the pressure of gas in patient circuit 58 is controlled, for example, by controlling the motor speed of flow generator 52.

Pressure support system 48 further includes flow sensor 62, which measures the flow of the breathing gas within delivery conduit 56. In the particular embodiment shown in the example of FIG. 2, flow sensor 62 is interposed in line with delivery conduit 56, preferably downstream of valve 60. Flow sensor 62 generates a flow Signal $Q_{MEASURED}$ that is provided to controller 64 and is used by controller 64 to determine the flow of gas at patient 54. Of course, other techniques for measuring the respiratory flow of patient 54 are contemplated by the present invention such as, for example and without limitation, measuring the flow directly at patient 54 or at other locations along delivery conduit 56, measuring patient flow based on the operation of flow generator 52, and measuring patient flow using a flow sensor (not shown) upstream of valve 60. Controller 64 may be, for example and without limitation, a microprocessor, a microcontroller or any other known or suitable processing device, which includes or is operably coupled to a memory (not shown) that provides a storage medium for data and software executable by controller 64 for controlling the operation of pressure support system 48 and, in particular, CPAP machine 50.

Finally, as described in greater detail hereinbelow, pressure support system 48 includes user interface 66, which communicates input from the user (e.g., patient 54; clinician; caregiver) to controller 64 to adjust and/or set various parameters of CPAP machine 50 and/or accessory 70 therefor. User interface 66 also displays and/or outputs information and data to the user. In the example embodiment shown in FIG. 2 (see also FIG. 4), accessory 70 is a humidifier. Housing 71 of humidifier 70 attaches to housing 51 of CPAP machine 50. It will, however, be appreciated that the use of other known or suitable accessories (not shown), other than or in addition to humidifier 70, is within the scope of the invention.

Figure 4:
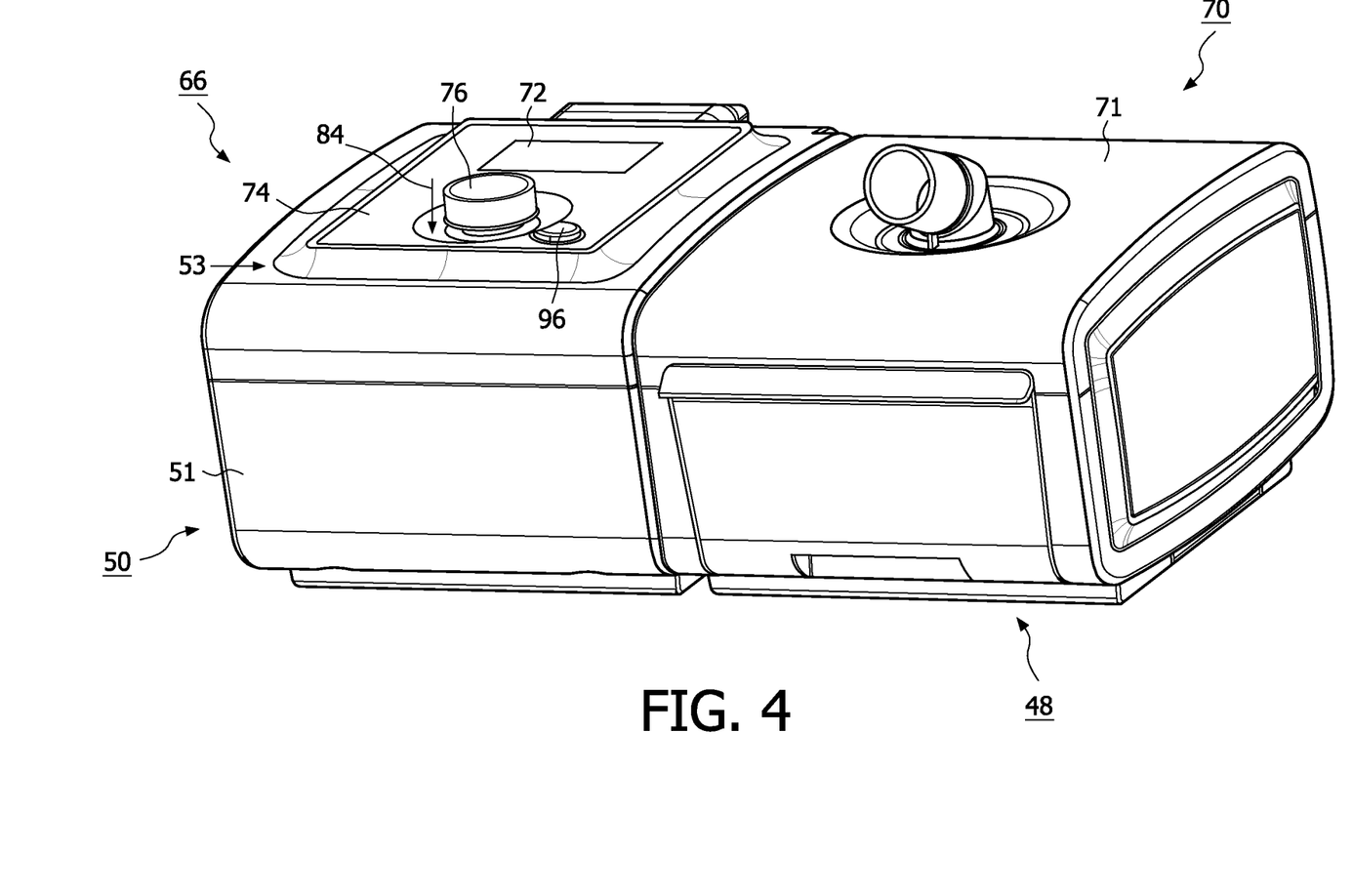
FIG. 4 is an isometric view of the pressure support device and user interface therefor of FIG. 3, modified to show a humidifier being employed therewith.

When humidifier 70 is coupled to CPAP machine 50, as shown in FIGS. 2 and 4, it is controlled (e.g., without limitation, adjusted; set) using the same user interface 66 as CPAP machine 50. Accordingly, unlike conventional pressure support systems (see, for example, CPAP machine 1 and humidifier 15 of FIG. 1, each of which has its own separate controller (not shown), and its own separate user interface 5 and 27, respectively), in accordance with the present invention, single user interface 66 communicates with controller 64 to control both CPAP machine 50 independently and in combination with humidifier 70.

Figure 3:
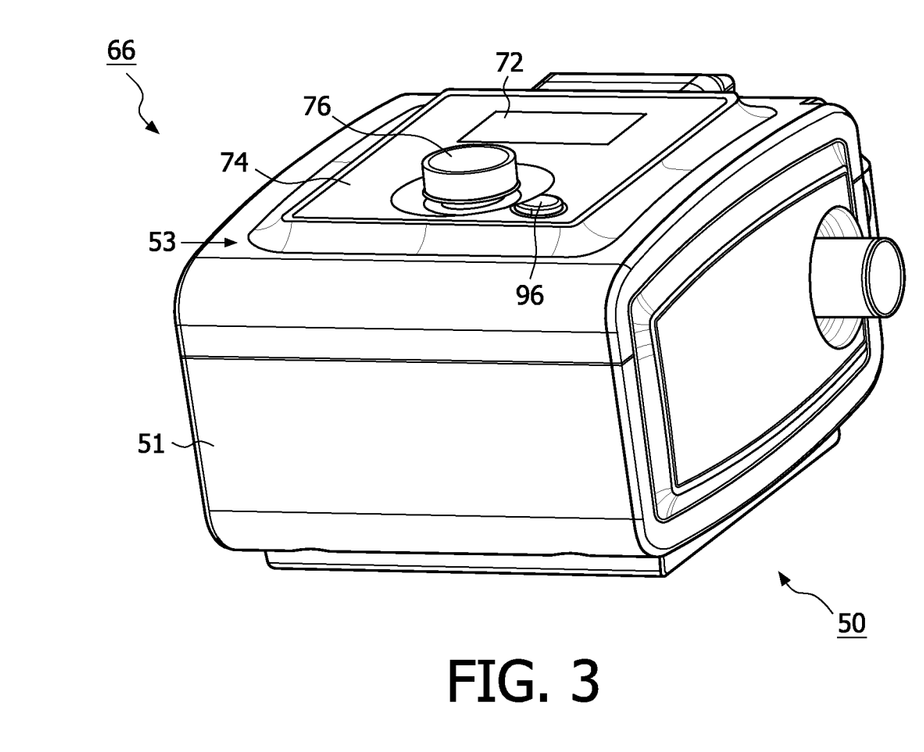
FIG. 3 is an isometric view of a pressure support device and user interface therefor, in accordance with one non-limiting example embodiment of the invention.

FIG. 3 shows CPAP machine 50 without humidifier 70, whereas FIG. 4 shows CPAP machine 50 with humidifier 70, thereby further illustrating the fact that the aforementioned controller 64 (FIG. 2) is adapted to operate CPAP machine 50 independently, as shown in FIG. 3, or in combination with a suitable accessory such as, for example and without limitation, the humidifier 70 shown in FIG. 4. A non-limiting particular embodiment of user interface 66 in accordance with the present invention, is also shown. Specifically, user interface 66 is accessible from exterior 53 of CPAP machine housing 51, and includes primary display 72, secondary display 74 and single control 76. As will be described in greater detail hereinbelow, secondary display 74 is a dead front on the exterior 53 of CPAP machine housing 51. Single control 76, which in the example shown and described herein is a single control knob, extends outwardly from housing 51 generally perpendicular to dead front 74, as shown. Primary display 72 is also disposed on the exterior 53 of housing 51, proximate to the single control knob 76. It will be appreciated that although a single control knob 76 that is pivotable and depressible is described herein for purposes of illustration, that any known or suitable alternative single control (not shown) could be employed without departing from the scope of the invention. For example and without limitation, a touch pad, a slider (e.g., horizontal; vertical), a switch, and a voice activated control could be employed. It will also be appreciated that the user interface 66 and displays 72,74 and single control 76 thereof could comprise a separate control mode (e.g., without limitation, multi-functional remote) (not shown) as opposed to being disposed on the CPAP machine housing 51 as shown and described herein.

Figure 5:
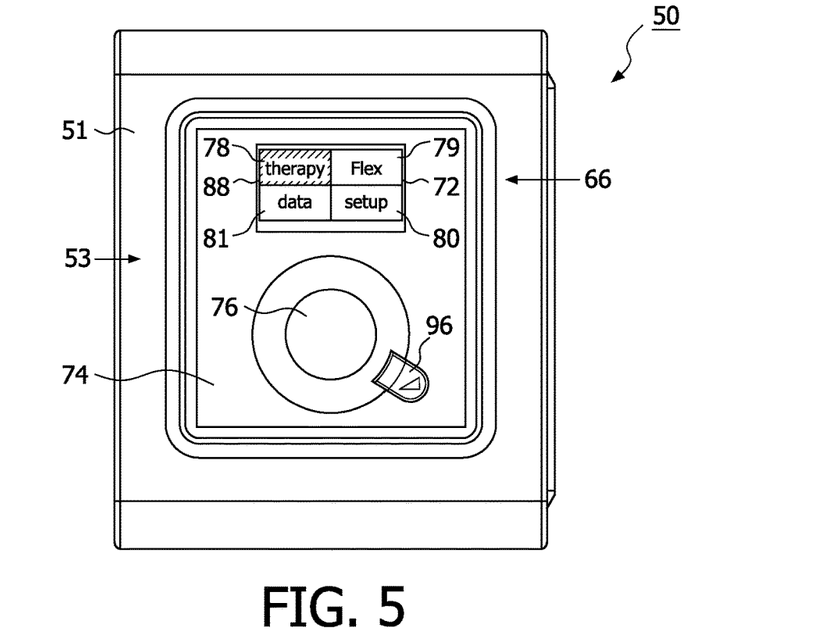
FIG. 5 is a top plan view of the user interface of FIG. 4, shown in a first mode of operation in accordance with one non-limiting example embodiment of the invention.
Figure 6:
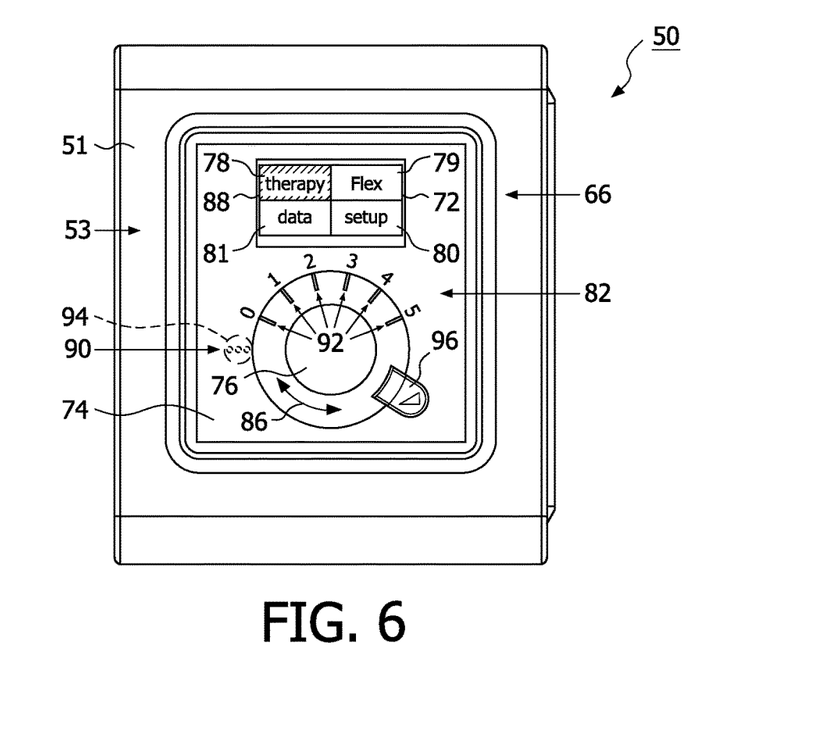
FIGS. 6 and 7 are top plan views of the user interface of FIG. 5, modified to illustrate operation of a dead front display in a second mode of operation in accordance with non-limiting example embodiments of the invention.
Figure 7:
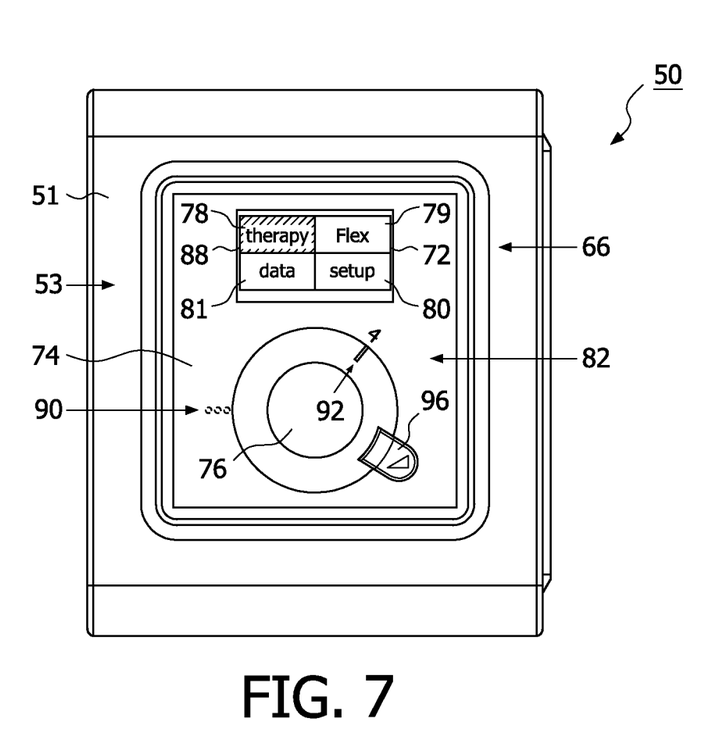
Figure 8:
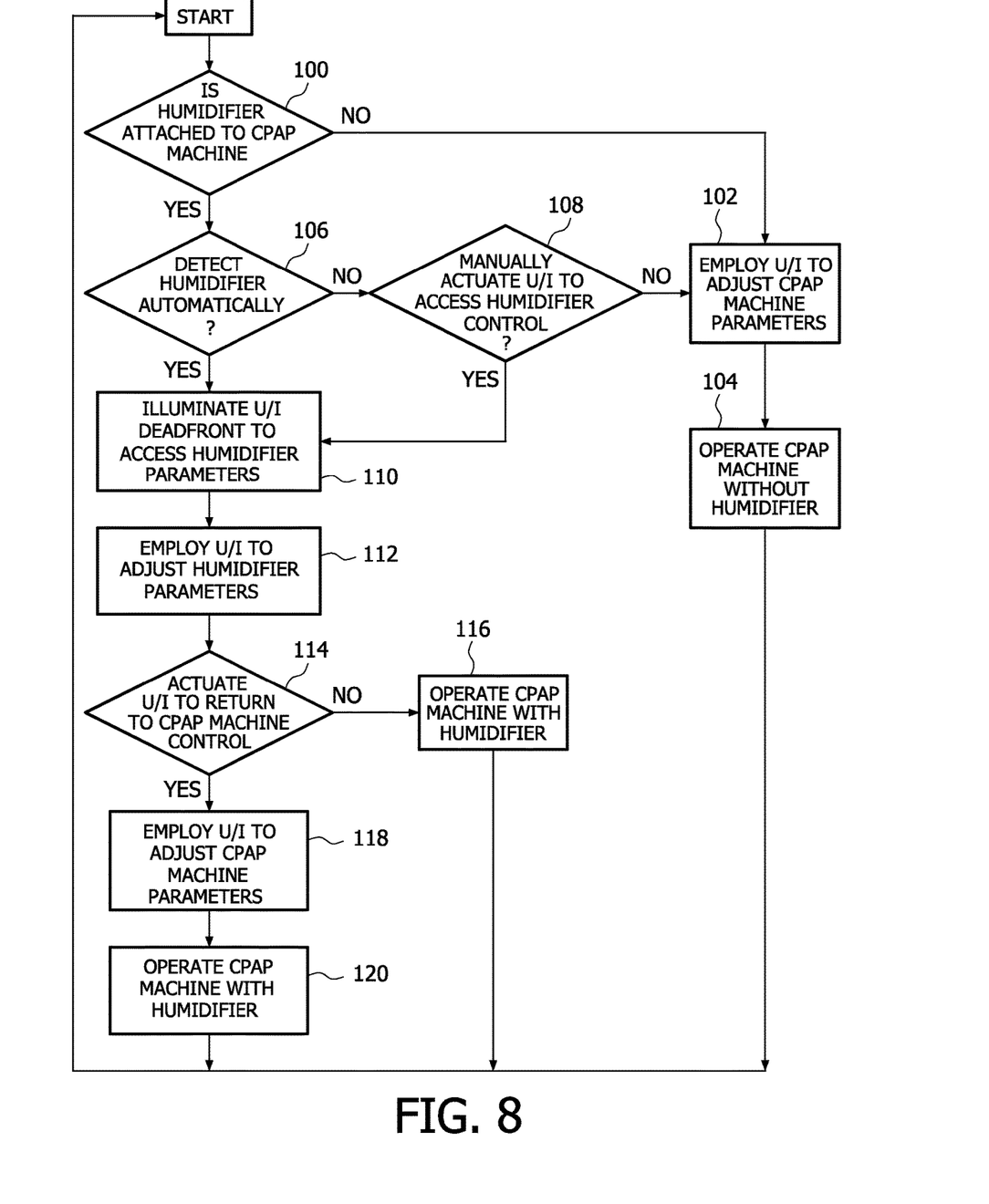
FIG. 8 is a flow diagram of a method of operating a pressure support device in accordance with one non-limiting example embodiment of the invention.

Single control knob 76 is operable in one mode of operation (e.g., without limitation, a first mode of operation), shown in FIG. 5, to adjust and/or select operating parameters 78,79,80,81 of CPAP machine 50, and in another mode of operation (e.g., without limitation, a second mode of operation), shown in FIGS. 6 and 7, to adjust and/or select operating parameter(s) 82 of humidifier 70. As shown, for example, by comparing FIG. 5 to FIGS. 6 and 7, it will be appreciated that dead front 74 is operational only in the second mode of operation. Of course, it will be appreciated that although only first and second modes of operation are described herein for economy of disclosure, that the user interface 66 may be operable in any known or suitable alternative number of modes. More specifically, as shown in FIG. 5, dead front 74 appears as a substantially blank portion (e.g., panel) of the exterior 53 of housing 51 in the first mode of operation. However, as shown in FIGS. 6 and 7, at least a portion of dead front 74 is illuminated in the second mode of operation to display various parameters (e.g., 82) associated with humidifier 70 (FIG. 4; humidifier 70 is not shown in FIGS. 6 and 7 for ease of illustration).

In the illustrative example of FIGS. 5-7, operating parameters 78, 79, 80, and 81, which are viewable on primary display 72, include therapy 78, Flex 79, setup 80 and data 81. Such operating parameters are generally well known and are available, for example, on the REMstar M Series of CPAP machines (illustrated, for example, in FIG. 1) manufactured by Philips Respironics of Murrysville, Pa. A primary indicator or indicia, such as cursor 88, is provided to facilitate navigation of primary display 72, for example, by highlighting the desired operating parameter 78, 79, 80, or 81. For example and without limitation, in FIGS. 5-7, cursor 88 is highlighting therapy parameter 78. Accordingly, it will be appreciated that primary display 72 of CPAP machine 50 displays and provides the ability to adjust and/or select well known pressure support functions.

By way of one non-limiting example, a user (e.g., patient; clinician; caregiver) could pivot (e.g., rotate clockwise or counterclockwise in the direction of arrow 86 of FIG. 6) single control knob 76 of user interface 66 in the first mode of operation to move cursor 88 to highlight the desired operating parameter 78, 79, 80, 81 of CPAP machine 50. Once highlighted, the desired parameter (e.g., without limitation, therapy 78) can then be selected, for example, by depressing single control knob 76 toward housing 51 in the direction of arrow 84 of FIG. 4. Once selected, the user can then employ single control knob 76 to adjust and set additional features associated with the particular operating parameter (e.g., 78) of CPAP machine 50. Accordingly, it will be appreciated that user interface 66 provides a wide range of functionality that can be suitably adjusted relatively quickly and easily by virtue of single control knob 76.

Additionally, when humidifier 70 is operably coupled to CPAP machine 50, as shown in FIG. 4, dead front 74 of user interface 66 is activated, as shown in FIGS. 6 and 7. Dead front 74 includes a number of secondary indicia 90,92, which in the illustrative embodiment of FIGS. 6 and 7 are illuminable characters, such as heated humidifier symbol 90 and numbers 92. Specifically, a number of illuminating elements 94 (e.g., without limitation, light bulbs; LEDs) of user interface 66 illuminate the corresponding illuminable characters 90,92 to be visible on dead front 74. For ease of illustration, only one illuminating element 94 is shown in simplified form in hidden line drawing in FIG. 6. It will be appreciated that illuminating elements 94 are disposed beneath dead front 74 and are activated only in the second mode of operation to illuminate the corresponding illuminable character (e.g., symbol 90). In the first mode of operation, illuminable elements 94 are inactive and, therefore, illuminable characters 90,92 are substantially invisible on dead front 74 such that dead front 74 appears substantially blank, as shown, for example, in FIG. 5. It will be appreciated that any known or suitable number, type and/or configuration of illuminating elements 94 could be employed to suitably illuminate dead front 74 in the second mode of operation, in accordance with the invention.

Accordingly, in the second mode of operation, the same single control knob 76 that was used to adjust operating parameters 78, 79, 80, 81 of CPAP machine 50 in the first mode of operation, is used to adjust and/or select operating parameter 82 (e.g., without limitation, humidity level) of humidifier 70 (FIG. 4; humidifier 70 is not shown in FIGS. 6 and 7 for ease of illustration). It will be appreciated that this may be accomplished, for example, by pivoting single control knob 76 clockwise or counterclockwise in the direction indicated by arrow 86 of FIG. 6 to select (e.g., illuminate) the desired number 92 and thus humidity level. For example and without limitation, in the illustrative embodiment of FIG. 7, humidity level 4 has been selected. The symbol 90 provides a readily visible indicator indicia to the user to indicate that a heated humidifying mode of operation is being implemented.

In addition to performing the aforementioned adjustment and selection functions, single control knob 76 is also depressible toward housing 51 in the direction of arrow 84 of FIG. 4, for example, to switch between the first mode of operation (FIG. 5) and second mode of operation (FIGS. 6 and 7). In this manner, the same single control knob 76 of the same single user interface 66, which is disposed on housing 51 of CPAP machine 50, is readily operable to adjust both CPAP machine 50 independently, and CPAP machine 50 in combination with any known or suitable accessory or plurality of accessories, such as humidifier 70.

It will be appreciated that in addition to single control knob 76, user interface 66 optionally includes at least one preset button 96 corresponding to a preprogrammed mode of therapy for the patient 54 (FIG. 2). For example and without limitation, in the illustrative embodiment of FIGS. 5-7, preset button 96 is included, which can be depressed to activate a ramp therapy, which is a generally well known preprogrammed gradually increasing pressure support therapy. Of course it will be appreciated that alternative or additional preset buttons (not shown) corresponding to any known or suitable alternative or additional preprogrammed mode(s) of therapy could be employed with user interface 66, without departing from the scope of the invention. It will further be appreciated that no such preset button 96 is required, but rather is optionally provided as a convenience feature to even further enhance the user-friendliness of the disclosed CPAP machine 50.

FIG. 7 is a flowchart showing a method of operating CPAP machine 50 (FIGS. 2-7) in accordance with a particular, non-limiting embodiment of the present invention. The method begins at step 100, with a determination of whether or not humidifier 70 (FIGS. 2 and 4) is attached to the CPAP machine 50. If not, then at step 102, user interface 66 and, in particular, single control knob 76 thereof, can be used in the first mode of operation to suitably adjust CPAP machine operating parameters 78,79,80,81. Then, at step 104, CPAP machine 50 can be operated without the humidifier (see, for example, FIGS. 3 and 5). Alternatively, at step 106, humidifier 70 may be detected automatically by the system controller 64 (FIG. 2). However, even if humidifier 70 is not detected automatically, dead front 74 (FIGS. 6 and 7) can nonetheless be manually actuated, at step 108, for example and without limitation, by depressing single control knob 76 toward CPAP machine housing 51 in the direction of arrow 84 of FIG. 4, as previously discussed hereinabove. Next, at step 110, dead front 74 of user interface 66 is illuminated to access humidifier operating parameters 82 (e.g., without limitation, humidity level) and, at step 112, the same user interface 66 and, in particular, the same single control knob 76 thereof is adjustable in the second mode of operation, clockwise or counterclockwise in the direction of arrow 86 of FIG. 6, to adjust humidifier parameter 82, as previously discussed hereinabove with respect to FIGS. 6 and 7.

After suitably adjusting humidifier 70 in the second mode of operation, at step 114 the user may optionally actuate (e.g., depress in the direction of arrow 84 of FIG. 4) single control knob 76 of user interface 66 to switch from the second mode of operation to the first mode of operation. If this is not done, for example, because CPAP machine 50 is already set as desired, then at step 116 CPAP machine 50 can be operated with humidifier 70 in accordance with the established settings. Alternatively, if the user does return to the first mode of operation at step 114, then at step 118, user interface 66 and, in particular, single control knob 76, can be adjusted (e.g., clockwise or counterclockwise in the direction of arrow 86 of FIG. 6) to adjust CPAP machine operating parameters 78, 79, 80, 81, as previously described with respect to FIG. 5. Then, at step 120, after both CPAP machine 50 has been suitably adjusted in the first mode of operation, and humidifier 70 has been suitably adjusted in the second mode of operation, CPAP machine 50 is operated in combination with humidifier 70.

Thus, as described in detail herein, the present invention provides a pressure support device 50 and method of operation for employing a single user interface 66 and, in particular, a single control 76 for efficiently and effectively adjusting operating parameters of both the pressure support device 50 independently, and the pressure support device 50 in combination with a suitable accessory 70. This advantageously eliminates the requirement for separate user interfaces and associated controls for the pressure support device 50 and accessory 70, thereby reducing the cost of the pressure support system 48. The single control 76 and unique dead front secondary display 74 also simplify operation of the system, making it substantially more user friendly than conventional multiple-control pressure support devices (see, for example, CPAP machine 1 of FIG. 1).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure support device adapted to produce a pressurized flow of breathing gas for delivery to a patient, the pressure support device comprising:
   a housing;
   a controller enclosed by the housing and being adapted to operate the pressure support device independently or in combination with an accessory, wherein the controller is configured to operate the pressure support device to produce a pressurized flow of breathing gas for delivery to the patient; and
   a user interface being operably coupled to the controller, the user interface comprising a primary display, a secondary display that is physically separate and spatially apart from the primary display, and a single control, the single control being operable in a first mode of operation to select and adjust a number of operating parameters of the pressure support device, and in a second mode of operation to select and adjust a number of operating parameters of the accessory, the secondary display being operational in response to the single control being operated in the second mode of operation and being non-operational in response to the control being operated in the first mode of operation, such that the entire secondary display is always substantially blank responsive to the single control being operated in the first mode of operation, wherein the primary display is configured to display a number of primary indicia indicative of corresponding ones of the operating parameters of the pressure support device, wherein the secondary display is configured to display a number of secondary indicia indicative of corresponding ones of the operating parameters of the accessory, wherein the secondary indicia include illuminable characters disposed on the secondary display, and wherein the pressure support device is configured to provide therapy to the patient during the first and second mode of operation.

2. The pressure support device of claim 1, wherein the single control of the user interface is a single control knob movably coupled to the housing of the pressure support device; wherein the single control knob is depressible toward the housing to switch between the first mode of operation and the second mode of operation; and wherein the single control knob is pivotable clockwise and counterclockwise to adjust a corresponding one of the operating parameters of the pressure support device in the first mode of operation and a corresponding one of the operating parameters of the accessory in the second mode of operation.

3. The pressure support device of claim 1, wherein the primary display is an electronic display.

4. The pressure support device of claim 3, wherein the secondary display is a dead front in the first mode of operation; wherein the user interface further comprises illuminating elements; wherein in the first mode of operation the illuminating elements are inactive and the illuminable characters are substantially invisible on the secondary display; and wherein in the second mode of operation at least one of the illuminating elements is activated to illuminate a corresponding at least one of the illuminable characters to be visible on the secondary display.

5. The pressure support device of claim 4, wherein the single control is a single control knob extending outwardly from the secondary display; wherein in the second mode of operation the single control knob is pivotable clockwise and counterclockwise to select a corresponding one of the illuminable characters of the secondary display, thereby making an associated adjustment of a corresponding one of the operating parameters of the accessory.

6. The pressure support device of claim 5, wherein the illuminable characters of the secondary display include at least one symbol and a plurality of numbers; wherein the at least one symbol identifies the accessory by type; wherein the numbers correspond to an amplitude of the corresponding one of the operating parameters of the accessory; and wherein the numbers are disposed radially with respect to the single control knob.

7. The pressure support device of claim 4, wherein the housing of the pressure support device includes an exterior; wherein the secondary display is disposed on the exterior; wherein the single control extends outwardly from the housing perpendicularly to the secondary display; and wherein the primary display is disposed on the exterior of the housing proximate to the single control.

8. The pressure support device of claim 1, wherein the pressure support device is a CPAP machine; wherein the accessory is a humidifier; wherein the humidifier is adapted to be operably coupled to the housing of the CPAP machine; wherein the second mode of operation corresponds to operation of the CPAP machine in combination with the humidifier; wherein in the first mode of operation the single control of the user interface controls operating parameters of the CPAP machine; and wherein in the second mode of operation, the single control of the user interface controls operating parameters of the humidifier.

9. The pressure support device of claim 1, wherein the user interface further comprises at least one preset button corresponding to a preprogrammed mode of therapy for the patient.

10. A method of operating a pressure support device to produce a pressurized flow of breathing gas for delivery to a patient, the method comprising:
   operably coupling an accessory to the pressure support device, wherein the pressure support device produces a pressurized flow of breathing gas for delivery to the patient;

actuating a user interface disposed on a housing of the pressure support device, the user interface comprising a primary display, a secondary display that is physically separate and spatially apart from the primary display, and a single control, the primary display including one or more primary indicia indicative of one or more operating parameters of the pressure support device in a first mode of operation, the secondary display including one or more secondary indicia indicative of one or more operating parameters of the accessory in a second mode of operation, the secondary display being operational in response to the single control being operated in the second mode of operation and being non-operational in response to the control being operated in the first mode of operation, such that the entire secondary display is always substantially blank responsive to the single control being operated in the first mode of operation, wherein the primary display includes a number of primary indicia indicative of corresponding ones of the operating parameters of the pressure support device, wherein the secondary display includes a number of secondary indicia indicative of corresponding ones of the operating parameters of the accessory, wherein the secondary indicia include illuminable characters disposed on the secondary display, and wherein the pressure support device provides therapy to the patient during the first and second mode of operation; and manipulating the single control of the user interface, the single control being operable to: (a) adjust and select a corresponding one of the one or more operating parameters of the pressure support device in the first mode of operation, (b) adjust and select a corresponding one of the one or more operating parameters of the accessory in the second mode of operation, and (c) switch between the first mode of operation and the second mode of operation.

11. The method of claim 10, wherein
the secondary display of the pressure support device is a dead front,
wherein the user interface further includes one or more illuminating elements, the method further comprising:
illuminating at least one of the one or more illuminating elements in the second mode of operation to illuminate a corresponding one of the one or more illuminable characters to be visible on the secondary display.

12. The method of claim 10, wherein
the single control of the user interface is a single control knob movably coupled to the housing of the pressure support device, the method further comprising:
pivoting the single control knob clockwise and counter-clockwise to adjust the corresponding one of the one or more operating parameters of the pressure support device in the first mode of operation,
pivoting the single control knob clockwise and counter-clockwise to adjust the corresponding one of the one or more operating parameters of the accessory in the second mode of operation, and
depressing the single control knob toward the housing of the pressure support device to switch between the first mode of operation and the second mode of operation.

13. The method of claim 10, wherein
the pressure support device is a CPAP machine,
wherein the accessory is a humidifier, the method further comprising:
operably coupling the humidifier to the CPAP machine.

14. The method of claim 13, further comprising:
adjusting the single control of the user interface in the first mode of operation to adjust a corresponding one of the one or more operating parameters of the CPAP machine, and
adjusting the single control of the user interface in the second mode of operation to adjust a corresponding one of the one or more operating parameters of the humidifier.

15. The method of claim 10, further comprising:
actuating a preset button of the user interface to initiate a preprogrammed mode of therapy for a patient.

16. The method of claim 10, further comprising:
automatically detecting the accessory being operably coupled to the pressure support device, and
responsive to detecting the accessory, activating the secondary display of the user interface.

* * * * *